United States Patent
Kim (10) Patent No.: US 10,322,232 B2
(45) Date of Patent: *Jun. 18, 2019

(54) REGULATOR FOR DRUG INFUSION AND DRUG INFUSION DEVICE INCLUDING SAME

(71) Applicant: Young Mu Kim, Incheon (KR)

(72) Inventor: Young Mu Kim, Incheon (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/854,644

(22) Filed: Dec. 26, 2017

(65) Prior Publication Data

US 2018/0117246 A1 May 3, 2018

Related U.S. Application Data

(63) Continuation of application No. 14/903,595, filed as application No. PCT/KR2014/004689 on May 27, 2014, now Pat. No. 9,987,424.

(30) Foreign Application Priority Data

Jul. 9, 2013 (KR) .................. 10-2013-0080050

(51) Int. Cl.
   *A61M 5/168* (2006.01)
   *F16K 99/00* (2006.01)

(52) U.S. Cl.
   CPC .... *A61M 5/16813* (2013.01); *A61M 5/16881* (2013.01); *F16K 99/0015* (2013.01); *F16K 2099/0086* (2013.01)

(58) Field of Classification Search
   CPC ............ A61M 5/16813; A61M 5/16881
   See application file for complete search history.

(56) References Cited

U.S. PATENT DOCUMENTS

| 5,009,251 A | 4/1991 | Pike et al. |
| 5,019,047 A | 5/1991 | Kriesel |

(Continued)

FOREIGN PATENT DOCUMENTS

| EP | 0105738 | 4/1984 |
| JP | 11-505753 A | 5/1999 |

(Continued)

*Primary Examiner* — Laura A Bouchelle
(74) *Attorney, Agent, or Firm* — Haynes and Boone, LLP (57) ABSTRACT

The present invention provides a regulator for medicine infusion capable of preventing a flow rate of a liquid medicine to be injected to a patient from exceeding a predetermined flow rate needed for a patient, and controlling the flow rate of the liquid medicine to be uniformly maintained. The regulator for medicine infusion of the present invention provides the advantages of blocking and continuing the inflow of the liquid medicine by the combination of the elements of the membrane member, the resilient plate and the lever and by the adjusted resilience of the resilient plate, and allowing the liquid medicine to flow at a constant rate by adjusting the resilience of the resilient plate and/or the resilience of the membrane member at predetermined levels. In addition, the regulator for medicine infusion of the present invention provides the advantages of controlling the flow rate of the liquid medicine to be injected to a patient to be uniformly maintained, and being applicable to intravenous bottles or various medicine injectors and being easily installed in them.

18 Claims, 7 Drawing Sheets

(56) References Cited

U.S. PATENT DOCUMENTS

| | | | |
|---|---|---|---|
| 5,178,182 A * | 1/1993 | Kamen | A61M 5/16809 |
| | | | 137/454.2 |
| 5,697,153 A | 12/1997 | Saaski et al. | |
| 5,797,586 A | 8/1998 | Schulte | |
| 5,957,895 A | 9/1999 | Sage et al. | |
| 6,619,308 B2 | 9/2003 | Massengale et al. | |
| 8,512,287 B2 | 8/2013 | Cindrich et al. | |
| 9,987,424 B2 * | 6/2018 | Kim | A61M 5/16813 |
| 2003/0167035 A1 | 9/2003 | Flaherty et al. | |
| 2005/0187515 A1 | 8/2005 | Varrichio et al. | |
| 2005/0267422 A1 | 12/2005 | Kriesel | |
| 2007/0051409 A1 | 3/2007 | Landy, III et al. | |
| 2007/0156090 A1 | 7/2007 | Kriesel | |
| 2007/0219480 A1 | 9/2007 | Kamen et al. | |
| 2008/0091150 A1 | 4/2008 | Murphy et al. | |
| 2010/0069830 A1 | 3/2010 | Grigorov | |
| 2011/0009814 A1 | 1/2011 | Tsoukalis | |
| 2011/0190694 A1 | 8/2011 | Lanier, Jr. et al. | |
| 2011/0282276 A1 | 11/2011 | Abal | |
| 2016/0089070 A1 | 3/2016 | Russ et al. | |

FOREIGN PATENT DOCUMENTS

| | | |
|---|---|---|
| JP | 2012-500035 A | 1/2012 |
| KR | 10-2007-0027675 A | 3/2007 |
| KR | 10-2012-0025673 A | 3/2012 |

* cited by examiner

REGULATOR FOR DRUG INFUSION AND DRUG INFUSION DEVICE INCLUDING SAME

CROSS-REFERENCE TO RELATED APPLICATIONS

This patent application is a continuation of U.S. patent application Ser. No. 14/903,595 filed on Jan. 7, 2016, which is a U.S. national stage continuation application under 35 U.S.C. § 371 of International Patent Application No. PCT/KR2014/004689 filed on May 27, 2014, which claims the benefit of Korean Patent Application No. 10-2013-0080050 filed on Jul. 9, 2013.

The entire contents of all of the above-mentioned patent applications are hereby expressly incorporated by reference in their entirety.

TECHNICAL FIELD

The present invention relates to a regulator for medicine infusion and a medicine infusion device including the same, and more particularly, to a regulator for medicine infusion capable of preventing a flow rate of a liquid medicine to be injected to a patient from exceeding a predetermined flow rate needed for a patient, and controlling the flow rate of the liquid medicine to be uniformly maintained, and a medicine infusion device including the same.

Moreover, the present invention relates to a regulator for medicine infusion which can control a flow rate of a liquid medicine to be injected to a patient to be uniformly maintained, and which is capable of being applied to intravenous bottles or various medicine injectors and is easily installed in them, and a medicine infusion device including the same.

BACKGROUND ART

In general, when a medicine stored in an intravenous bottle (e.g. Ringer bottle) or the like is injected into a patient's blood vessel, the medicine is injected into the patient's blood vessel at a flow rate which can be varied according to a storage amount of the medicine. In this regard, when it is necessary to inject a liquid medicine such as a special injection medicine, including an anti-cancer medicine or an antibiotic, to a patient, the desired amount thereof should be injected consistently and continuously depending on a patient's condition. If the amount of special injection medicine necessary for a patient is not consistently and continuously injected, there is a risk of the occurrence of shock.

In a conventional regulator for regulating a flow rate of a liquid medicine, the regulator is generally rotated upward or downward to change a cross-sectional area of a tube, thereby regulating the amount of liquid medicine flowing to a syringe needle. However, the conventional regulator has a problem in that it is difficult to finely regulate the flow rate of liquid medicine.

In consideration of such a problem, PCT Patent Publication No. WO 03/066138 A1 discloses a liquid supply apparatus for pushing out a liquid medicine contained in a cylinder by a piston to inject the liquid medicine to a patient. In order to inject the liquid medicine to the patient consistently and continuously, the liquid supply apparatus includes a gas supply apparatus which generates gas and applies a constant pressure of the generated gas against a piston to gradually push the piston, and a pressure regulating valve which can uniformly regulate the pressure of the generated gas in the gas supply apparatus by discharging high pressure outside which may be temporarily generated from the gas supply apparatus.

The liquid supply apparatus is excellent, but it can be improved further in common with other excellent technologies. That is, the conventional liquid supply apparatus has a need for improvement in that it is inconvenient to install the pressure regulating valve inside the gas supply apparatus and in that manufacturing cost is increased due to a complicated structure of the pressure regulating valve. Moreover, the pressure regulating valve has a limit in application to various medicine injection devices because it can be applied only to medicine injection devices each of which has a gas supply apparatus for generating gas.

Therefore, in the technical field of the present invention, there are unceasing demands on the improvement of a medicine flow rate regulator, which can prevent a flow rate of a liquid medicine to be injected to a patient from exceeding a predetermined flow rate needed for a patient and control the flow rate of the liquid medicine to be uniformly maintained, and can be applied to intravenous bottles or various medicine injectors and be easily installed in them.

SUMMARY OF INVENTION

Accordingly, the present invention has been made in an effort to solve the above-mentioned problems occurring in the prior arts, and it is an object of the present invention to provide a regulator for medicine infusion which can prevent a flow rate of a liquid medicine to be injected to a patient from exceeding a predetermined flow rate needed for a patient and control the flow rate of the liquid medicine to be uniformly maintained, and a medicine infusion device including the same.

It is another object of the present invention to provide a regulator for medicine infusion which can control a flow rate of a liquid medicine to be injected to a patient to be uniformly maintained, and which is capable of being applied to intravenous bottles or various medicine injectors and is easily installed in them, and a medicine infusion device including the same.

DETAILED DESCRIPTION OF INVENTION

To achieve the above objects, the present invention provides a regulator for medicine infusion comprising:

a housing having an inlet communicating with an inflow conduit which extends to communicate with a liquid medicine storage space, an outlet communicating with an outflow conduit, and an internal space communicating with the inlet and the outlet;

a membrane member being located in the internal space of the housing and forming a medicine flow passage between the inlet and the outlet, the membrane member receiving a pressure of a liquid medicine discharged via the medicine flow passage from the inlet to the outlet and the shape of the membrane member being changed depending on a flow rate of the liquid medicine discharged via the medicine flow passage from the inlet to the outlet;

a lever being located below the membrane member and having an inlet side extension portion and an outlet side extension portion opposed to each other with respect to a rotary axis, the inlet side extension portion in contact with a lower surface of the membrane member and rotating on the rotary axis, according to the flow rate of the liquid medicine discharged via the medicine flow passage from the inlet to the outlet, to change the shape of the membrane member so that the shape changed membrane member blocks or opens the inlet; and a resilient plate being located between the membrane member and the lever and being in close contact with both the membrane member and the lever, the resilience of the resilient plate being adjusted at a predetermined level so as to allow the pressure of the liquid medicine received through the membrane member to be delivered to the outlet side extension portion of the lever only when the flow rate of the liquid medicine exceeds a predetermined flow rate needed for a patient.

In one embodiment of the regulator for medicine infusion according to the present invention, when the flow rate of the liquid medicine exceeds a predetermined flow rate needed for a patient, the pressure of the liquid medicine received through the membrane member overcomes the adjusted resilience of the resilient plate, and moves the outlet side extension portion of the lever downward and thus moves the inlet side extension portion of the lever upward so that the inlet side extension portion of the lever presses the inlet side of the membrane member upward and change the shape of the inlet side of the membrane member to block the inlet.

Meanwhile, when the liquid medicine is not introduced into the medicine flow passage after blocking of the inlet, the pressure of the liquid medicine is not further applied to the membrane member, and then the resilient plate applies an upward force, i.e. a resiliently restoring force to the membrane member so that the downward force applied to the outlet side extension portion of the lever is released. Accordingly, by the principle of the seesaw, the inlet side extension portion of the lever moves downward and the outlet side extension portion of the lever moves upward so as to release the upward force pressing the inlet side of the membrane member. In addition, when the liquid medicine is introduced from the inlet into the medicine flow passage, the shape changed inlet side of the membrane member is restored to its original position and shape by the inflow force of the liquid medicine.

In one embodiment of the regulator for medicine infusion according to the present invention, the housing may include an upper housing and a lower housing, which are detachably coupled. For example, the lower housing may be tightly fitted into a space formed by a lower wall of the upper housing extending downward in a vertical direction. From top to bottom, the membrane member, the resilient plate and the lever are located inside a space formed between the upper housing and the lower housing.

The upper housing may be configured to form an inflow passage between the inlet and the medicine flow passage and to form an outflow passage between the outlet and the medicine flow passage. According to the formation of the inflow passage and the outflow passage of the upper housing, the respective parts of the upper housing corresponding to the inflow passage and the outflow passage may take a protruding shape upward. The inflow conduit and the outflow conduit may be inserted into the inflow passage and the outflow passage, respectively. Preferably, the inflow passage and the outflow passage are vertically spaced apart from the medicine flow passage, and more preferably the inflow passage and the outflow passage are vertically connected to the medicine flow passage through a medicine inflow hole and a medicine outflow hole respectively which are formed opposite to each other in the upper housing.

In one embodiment of the regulator for medicine infusion according to the present invention, after the membrane member is seated on a peripheral portion of the lower housing, a peripheral portion of the membrane member is located and fixed between the upper housing and the lower housing when the lower housing is tightly fitted into the space formed by the lower wall of the upper housing extending downward in a vertical direction. Preferably, the shape of the membrane member is formed to correspond with that of the lower housing, and the peripheral portion of the membrane member protrudes upward and downward to be firmly fixed by fitting the protrusion into a space between the peripheral portion of the lower housing and a lower surface of the upper housing.

The membrane member may be divided into an inlet side portion and an outlet side portion, and the inlet side portion of an approximately circular shape may be partially overlapped with the outlet side portion of an approximately circular shape. In this instance, a boundary protrusion portion may be formed between the inlet side portion and the outlet side portion of the membrane member. The boundary protrusion portion becomes a boundary line for dividing the membrane member into the inlet side portion and the outlet side portion which are different from each other in area and thickness. Further, the boundary protrusion portion becomes a transformation point for receiving a force when the shape of the membrane member is changed by the pressure of the liquid medicine introduced into the medicine flow passage during the medicine infusion.

Particularly, in order to make the pressure of the introduced liquid medicine to be biasedly applied to the outlet side extension portion of the lever, the area of the outlet side portion of the membrane member may be formed to be larger than that of the inlet side portion of the membrane member, and/or the outlet side portion of the membrane member may be formed to be thicker than the inlet side portion of the membrane member.

In one embodiment of the regulator for medicine infusion according to the present invention, the lever may have a rotary shaft, and the rotary shaft may be bridged and joined on a pair of lever holders which are opposed to each other on a floor surface of the lower housing. After the rotary shaft of the lever is bridged and joined on the lever holders, the inlet side extension portion and the outlet side extension portion of the lever can move upward and downward about the rotary shaft. Since a protrusion is extended upward at an end of the inlet side extension portion, the inlet side extension portion can effectively deliver a force upward when in contact with a lower surface of the inlet side portion of the membrane member. Moreover, a protrusion may be also extended upward near an end of the outlet side extension portion. In this case, the outlet side extension portion can effectively receive the pressure of the liquid medicine through the outlet side portion of the membrane member and the resilient plate.

In one embodiment of the regulator for medicine infusion according to the present invention, the resilient plate may be a plate spring. The resilient plate may include a peripheral portion, a central portion and a rib for connecting the peripheral portion and the central portion with each other. The resilient plate may be upward prominent in a state where the central portion is gentle like a general plate spring, but may be flat. In order to regulate the flow rate and pressure of the liquid medicine discharged via the medicine flow passage from the inlet to the outlet, the resilience of the resilient plate can be adjusted to a predetermined level by at least one selected from the group consisting of a material of the resilient plate, thickness of the resilient plate and thickness of the rib. Furthermore, the resilience of the membrane member can be adjusted to a predetermined level by thickness of the outlet side portion of the membrane member so as to additionally regulate the flow rate and pressure of the liquid medicine discharged via the medicine flow passage from the inlet to the outlet.

For instance, the resilient plate made of a plastic material is used in cases in which the pressure of the liquid medicine is regulated to a low pressure, but the resilient plate made of spring steel is used in cases in which the pressure of the liquid medicine is regulated to a high pressure. In addition, in order to regulate the flow rate and pressure of the liquid medicine, the resilience of the resilient plate and/or the resilience of the membrane member can be adjusted by thickness of the resilient plate, thickness of the rib of the resilient plate and/or thickness of the outlet side portion of the membrane member. In order to regulate a pressure of the liquid medicine to a high pressure, the resilient plate and/or the outlet side portion of the membrane member should be thicker or the rib of the resilient plate should be thicker. On the other hand, in order to regulate a pressure of the liquid medicine to a low pressure, the resilient plate and/or the outlet side portion of the membrane member should be thinner or the rib of the resilient plate should be thinner.

Therefore, the regulator for medicine infusion according to the present invention provides the advantages of blocking and continuing the inflow of the liquid medicine by the combination of the elements of the membrane member, the resilient plate and the lever and by the adjusted resilience of the resilient plate, and allowing the liquid medicine to flow at a constant rate by adjusting the resilience of the resilient plate and/or the resilience of the membrane member at predetermined levels.

In one embodiment of the regulator for medicine infusion according to the present invention, the membrane member is preferably made of silicone, the resilient plate is preferably made of a plastic material or spring steel, and other components, such as the upper housing, the lower housing and the lever, etc. are preferably made of a plastic material. However, it will be understood by those of ordinary skill in the art that the above-mentioned components of the present invention are not restricted to the aforesaid materials but may be made of various materials being known in the relevant fields and meeting the objects of the present invention.

Moreover, the medicine infusion device includes the regulator for medicine infusion according to the present invention.

Advantageous Effects

As described above, the regulator for medicine infusion according to the present invention can prevent a flow rate of a liquid medicine to be injected to a patient from exceeding a predetermined flow rate needed for a patient, and control the flow rate of the liquid medicine to be uniformly maintained.

Concretely, the regulator for medicine infusion according to the present invention provides the advantages of blocking and continuing the inflow of the liquid medicine by the combination of the elements of the membrane member, the resilient plate and the lever and by the adjusted resilience of the resilient plate, and allowing the liquid medicine to flow at a constant rate by adjusting the resilience of the resilient plate and/or the resilience of the membrane member at predetermined levels.

In addition, the regulator for medicine infusion according to the present invention can control a flow rate of a liquid medicine to be injected to a patient to be uniformly maintained, and can be applied to intravenous bottles or various medicine injectors and be easily installed in them.

EXAMPLES

Hereinafter, preferred embodiments according to the present invention will be described in detail with reference to the accompanying drawings. The following embodiments of the present invention are just to implement the present invention and are not intended to limit or restrict the scope of the present invention. Thus, those that can be easily contemplated by persons skilled in the art from the detailed description and examples of the present invention are interpreted to fall within the scope of the present invention. References cited herein are incorporated herein by reference.

Figure 1:
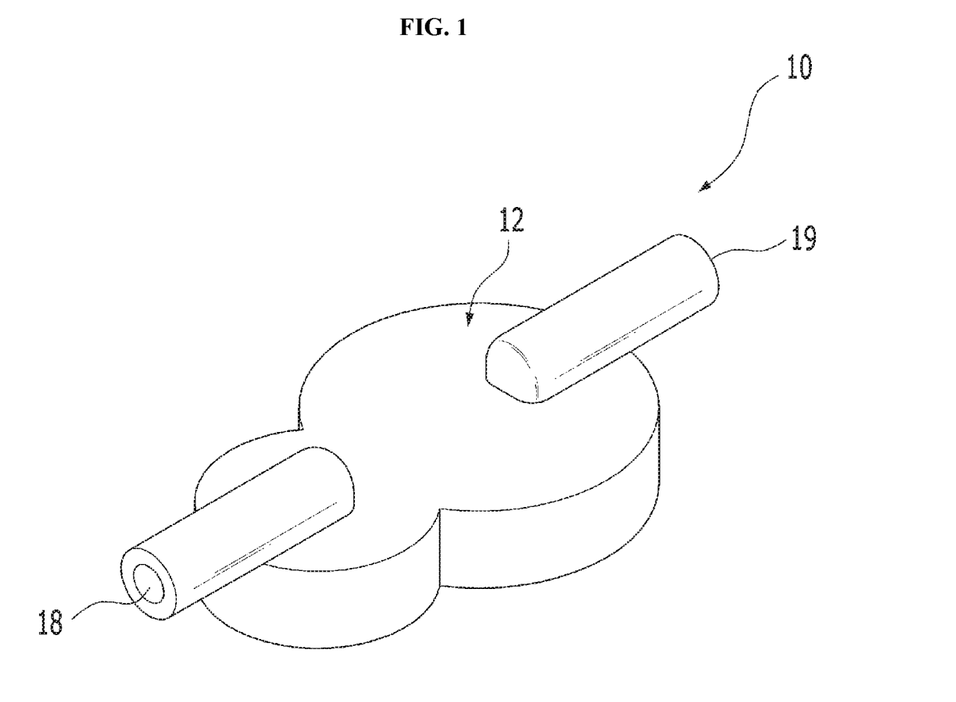
FIG. 1 is a perspective view showing a regulator for medicine infusion 10 in an assembled state according to an embodiment of the present invention.
Figure 2:
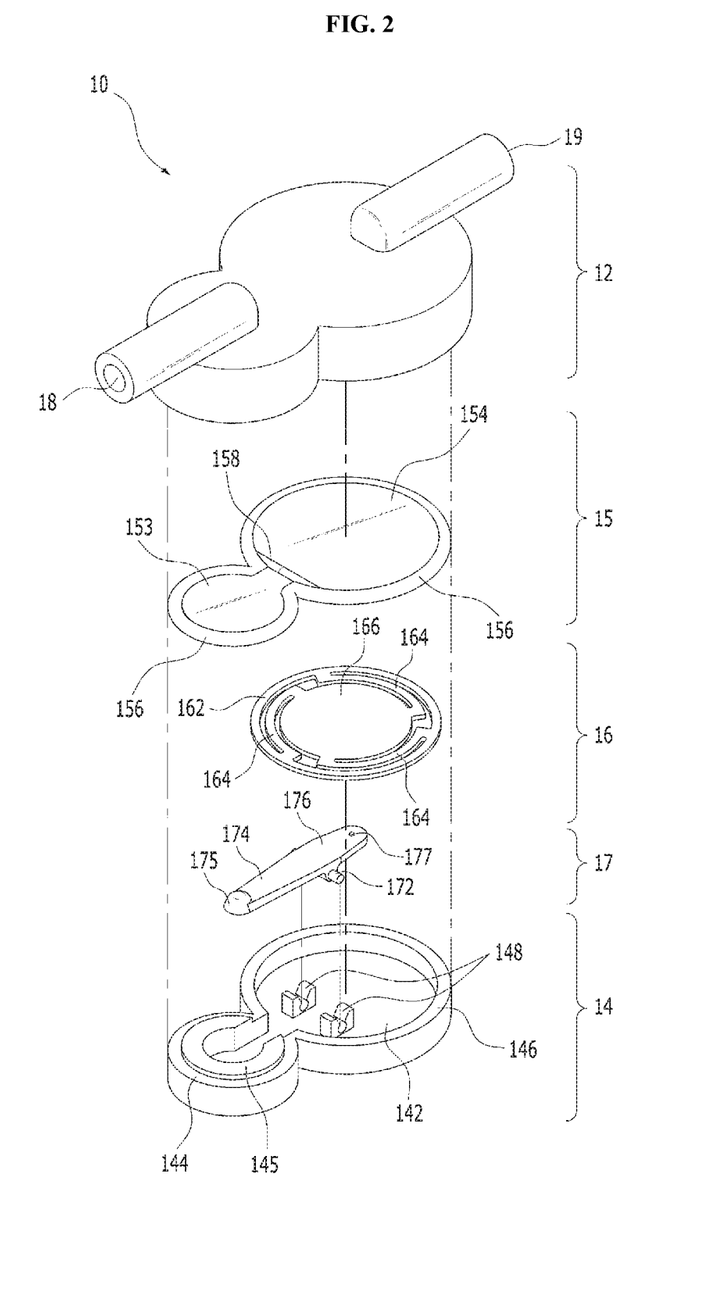
FIG. 2 is an exploded perspective view showing the regulator for medicine infusion 10 in a dissembled state according to an embodiment of the present invention.
Figure 3:
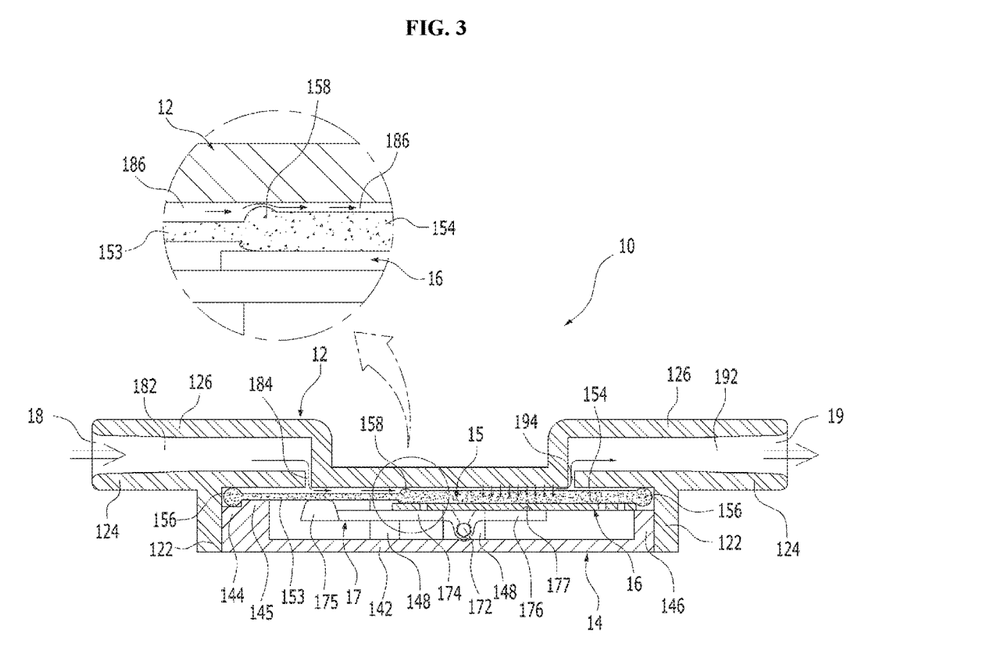
FIG. 3 is a longitudinal sectional view showing the regulator for medicine infusion 10 in an assembled state according to an embodiment of the present invention.

As shown in FIGS. 1 to 3, a regulator 10 for medicine infusion according to an embodiment of the present invention includes an upper housing 12, a lower housing 14, a membrane member 15, a resilient plate 16 and a lever 17.

The upper housing 12 and the lower housing 14 are detachably coupled to each other. For example, the lower housing 14 may be tightly fitted into a space formed by a lower wall 122 of the upper housing 12 extending downward in a vertical direction. As described above, when the upper housing 12 and the lower housing 14 are assembled, the entire housing is formed. From top to bottom, the membrane member 15, the resilient plate 16 and the lever 17 are located inside a space formed between the upper housing 12 and the lower housing 14.

As shown in FIG. 3, the assembly of the upper and lower housings 12 and 14 includes: an inlet 18 which communicates with an inflow conduit (not shown) extending to communicate with a medicine storage space (not shown); and an outlet 19 which communicates with an outflow conduit (not shown). The upper and lower housings 12 and 14 define a medicine flow passage 186 between the inlet 18 and the outlet 19 in association with the membrane member 15, which will be described later.

Figure 9:
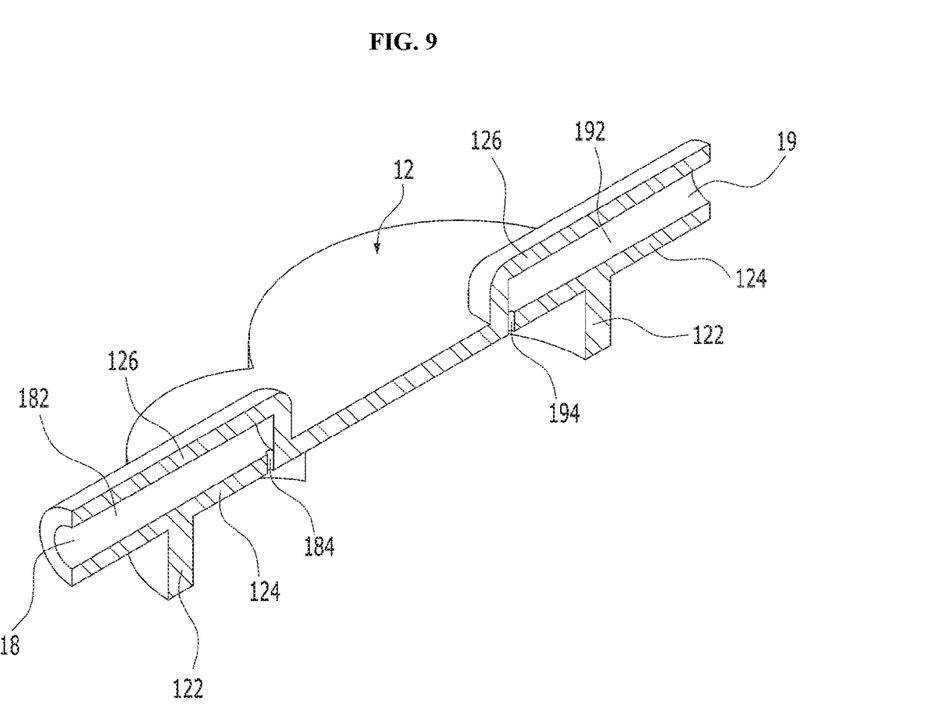
FIG. 9 is a longitudinal sectional view showing an upper housing of the regulator for medicine infusion 10 according to an embodiment of the present invention.

Furthermore, as shown in FIGS. 3 and 9, an upper plate 126 and a lower plate 124 of the upper housing 12 define an inflow passage 182 between the inlet 18 and the medicine flow passage 186, and define an outflow passage 192 between the outlet 19 and the medicine flow passage 186. According to the formation of the inflow passage 182 and the outflow passage 192 of the upper housing 12, the respective parts of the upper housing corresponding to the inflow passage 182 and the outflow passage 192 may take a protruding shape upward.

Not shown in the drawings, but the inflow conduit (not shown) and the outflow conduit (not shown) may be inserted into the inflow passage 182 and the outflow passage 192, respectively. Additionally, the inflow passage 182 and the outflow passage 192 are spaced apart from the medicine flow passage 186 in a vertical direction. The inflow passage 182 and the outflow passage 192 are vertically connected to the medicine flow passage 186 through a medicine inflow hole 184 and a medicine outflow hole 194 respectively, which are formed opposite to each other in the upper housing 12.

As shown in FIGS. 2 to 6, the membrane member 15 is seated on an inlet peripheral portion 144 of the lower housing 14 and an outlet peripheral portion 146 of the lower housing 14, and then, a peripheral portion 156 of the membrane member 15 is located and fixed between the upper housing 12 and the lower housing 14 when the lower housing 14 is tightly fitted into the space formed by the lower wall 122 of the upper housing 12 extending downward in a vertical direction. The shape of the membrane member 15 is formed to correspond to that of the lower housing 14, and the peripheral portion 156 of the membrane member 15 protrudes upward and downward to be firmly fixed by fitting the protrusion into a space formed between the peripheral portions 144 and 146 of the lower housing 14 and the lower plate 124 of the upper housing 12.

Additionally, the pressure of the liquid medicine discharged via the medicine flow passage 186 from the inlet 18 to the outlet 19 is delivered to the membrane member 15, and the membrane member 15 is preferably made of an elastic and flexible material which is transformable according to a flow rate and pressure of the liquid medicine discharged via the medicine flow passage 186 from the inlet 18 to the outlet 19. For instance, the membrane member 15 may be made of silicone. More preferably, the membrane member 15 is made of silicone in the form of a thin film.

The membrane member 15 may be divided into an inlet side portion 153 and an outlet side portion 154, and the inlet side portion 153 of an approximately circular shape may be partially overlapped with the outlet side portion 154 of an approximately circular shape. In this instance, a boundary protrusion portion 158 may be formed between the inlet side portion 153 and the outlet side portion 154 of the membrane member 15. The boundary protrusion portion 158 becomes a boundary line to divide the membrane member 15 into the inlet side portion 153 and the outlet side portion 154 which are different from each other in area and thickness. Further, the boundary protrusion portion 158 becomes a transformation point which receives a force when the shape of the membrane member 15 is changed by the inflow medicine pressure during the medicine infusion.

Particularly, in order to make the pressure of the introduced liquid medicine be biasedly applied to an outlet side extension portion 176 of the lever 17 which will be described later, the area of the outlet side portion 154 of the membrane member 15 may be formed to be larger than that of the inlet side portion 153 of the membrane member 15, and/or the outlet side portion 154 of the membrane member 15 is formed to be thicker than the inlet side portion 153 of the membrane member 15. In addition, the inlet side portion 153 of the membrane member 15 is supported by an extension portion 145 which is stepwise formed upwardly from the inlet side peripheral portion 144 of the lower housing 14 because it is relatively thinner than the outlet side portion 154 of the membrane member 15. The protruding peripheral portion 156 of the membrane member 15 is stably seated on the lower housing 14 while being caught to a stepped jaw formed by the inlet side peripheral portion 144 and the upward extension portion 145. In this instance, the upward extension portion 145 is stepped and protrudes from the inlet side peripheral portion 144 as much as a difference in thickness between the outlet side portion 154 and the inlet side portion 153 of the membrane member 15.

As shown in FIGS. 2 to 6, the lever 17 is located below the membrane member 15 and includes an inlet side extension portion 174 and an outlet side extension portion 176 which are opposed to each other with respect to a rotary shaft 172. The inlet side extension portion 174 comes in contact with the lower surface of the membrane member 15 and rotates on the rotary shaft 172 according to the flow rate of the discharged liquid medicine to change the shape of the membrane member 15 so that the shape changed membrane member 15 blocks or opens the medicine inflow hole 184.

In detail, the rotary shaft 172 of the lever 17 is bridged and joined on a pair of lever holders 148 which are opposed to each other on a floor surface 142 of the lower housing 14. After the rotary shaft 172 of the lever is bridged and joined on the lever holders 148, the inlet side extension portion 174 and the outlet side extension portion 176 of the lever move upward and downward about the rotary shaft 172. Since a protrusion 175 is extended upward at an end of the inlet side extension portion 174, the inlet side extension portion 174 can effectively deliver a force when in contact with a lower surface of the inlet side portion 153 of the membrane member 15. Moreover, a protrusion 177 is also extended upward near an end of the outlet side extension portion 176. In this case, the outlet side extension portion 176 can effectively receive the pressure of the liquid medicine through the outlet side portion 154 of the membrane member 15 and the resilient plate 16.

As shown in FIGS. 2 to 6, the resilient plate 16 is closely located between the membrane member 15 and the lever 17, and is seated over the outlet peripheral portion 146 of the lower housing 14 while covering a part of the inlet side extension portion 174 of the lever 17 and covering up the outlet side extension portion 176. Additionally, the resilient plate 16 includes a peripheral portion 162, a central portion 166 and a rib 164 which connects the peripheral portion 162 and the central portion 166 with each other. The resilient plate 16 may be upward prominent in a state where the central portion 166 is gentle like a general plate spring, but may be flat. It is preferable that the resilient plate 16 be a plate spring, but the present invention is not limited to the above.

In order to regulate the flow rate and pressure of the liquid medicine discharged via the medicine flow passage 186 from the inlet 18 to the outlet 19, the resilience of the resilient plate 16 can be adjusted to a predetermined level by at least one selected from the group consisting of a material of the resilient plate 16, thickness of the resilient plate 16 and thickness of the rib. Furthermore, the resilience of the membrane member 15 can be adjusted to a predetermined level by adjusting thickness of the outlet side portion 154 of the membrane member 15 so as to additionally regulate the flow rate and pressure of the liquid medicine discharged to the outlet 19.

For instance, the resilient plate 16 made of a plastic material is used in cases in which the pressure of the liquid medicine is regulated to a low pressure, but the resilient plate 16 made of spring steel is used in cases in which the pressure of the liquid medicine is regulated to a high pressure. In addition, in order to regulate the flow rate and pressure of the liquid medicine, the resilience of the resilient plate 16 and/or the resilience of the membrane member 15 can be adjusted by thickness of the resilient plate 16, thickness of the rib 164 of the resilient plate 16 and/or thickness of the outlet side portion 154 of the membrane member 15. In order to regulate the pressure of the liquid medicine to a high pressure, the resilient plate 16 and/or the outlet side portion 154 of the membrane member 15 should be thicker or the rib 164 of the resilient plate 16 should be thicker. On the other hand, in order to regulate the pressure of the liquid medicine to a low pressure, the resilient plate 16 and/or the outlet side portion 154 of the membrane member 15 should be thinner or the rib 164 of the resilient plate 16 should be thinner.

In the meantime, in the regulator 10 for medicine infusion according to an embodiment of the present invention, other components besides the membrane member 15 and the resilient plate 16 may be made of a plastic material. However, it will be easily understood by those of ordinary skill in the art that the present invention is not limited to the above and the components can be made of various materials being known in the art and meeting the objects of the present invention.

Figure 4:
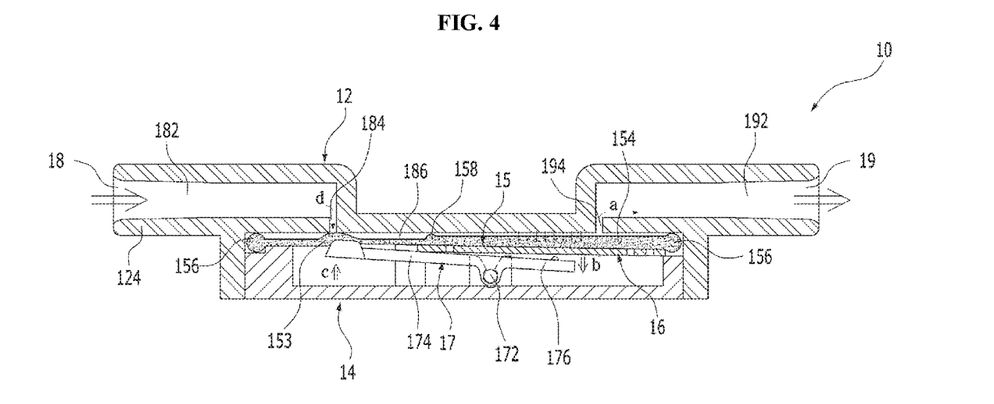
FIGS. 4 to 6 show use states for explaining operational processes of the regulator for medicine infusion 10 according to an embodiment of the present invention.
Figure 5:
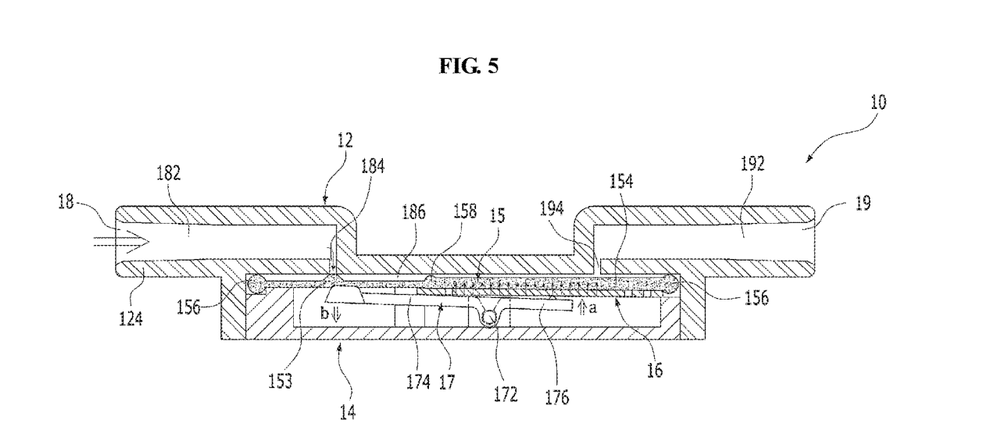
Figure 6:
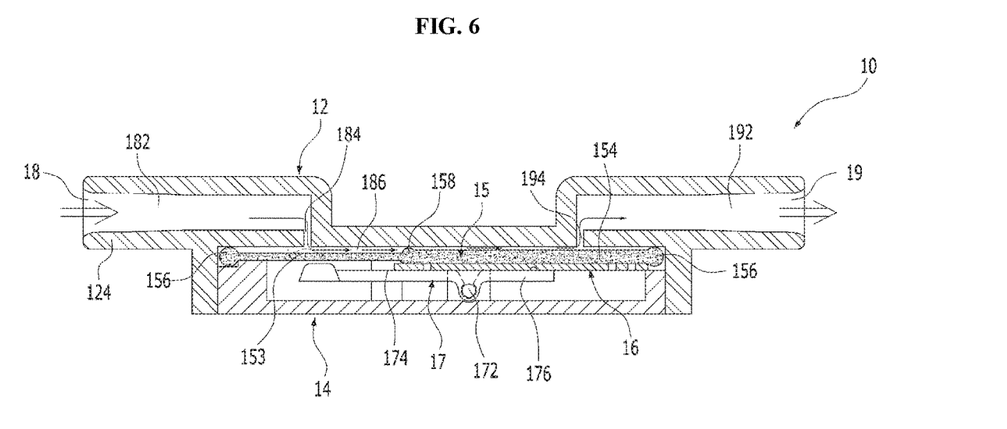

Referring to FIGS. 4 to 6, the operation of the regulator 10 for medicine infusion according to an embodiment of the present invention will be described as follows.

First, FIG. 4 illustrates a state where the flow rate of the liquid medicine exceeds the flow rate needed for a patient, namely, a state where the liquid medicine, having the flow rate of exceeding the adjusted pressure set by the resilience of the resilient plate 16 and/or the resilience of the membrane member 15, flows in and out (an excessive injection of liquid medicine). The liquid medicine introduced through the inlet 18, the inflow passage 182 and the medicine inflow hole 184 passes through the medicine flow passage 186 between the lower surface of the upper housing 12 and the upper surface of the inlet side portion 153 of the membrane member 15. The introduced liquid medicine makes a narrow space between the boundary protrusion portion 158 and the lower surface of the upper housing 12 to pass through the narrow space by the pressure of the liquid medicine running against the boundary protrusion portion 158. After that, the introduced liquid medicine flows into the medicine flow passage 186 between the lower surface of the upper housing 12 and the upper surface of the outlet side portion 154 of the membrane member 15, and then flows out through the medicine outflow hole 194 (See the state "a" in FIG. 4).

Since the outlet side portion 154 of the membrane member 15 is thicker than the inlet side portion 153, the space formed between the lower surface of the upper housing 12 and the upper surface of the outlet side portion 154 is narrower than the space formed between the lower surface of the upper housing 12 and the upper surface of the inlet side portion 153. In the above state, the liquid medicine passing through the narrower space applies stronger pressure to the outlet side portion 154 of the membrane member 15, when being discharged through the medicine outflow hole 194 to the outflow passage 192 and the outlet 19. Namely, the applied pressure of the outlet side portion of the membrane member is stronger than that of the inlet side portion of the membrane member. Further, in view of the total sum of pressure applied to the membrane member 15, the total pressure applied to the outlet side portion 154 is additionally larger than that of the inlet side portion 153 because the area of the outlet side portion 154 is wider than that of the inlet side portion 153.

By the structural characteristics of the membrane member 15, there is an imbalance between the pressure of the liquid medicine applied to the outlet side portion 154 and the pressure of the liquid medicine applied to the inlet side portion 153. The pressure of the liquid medicine is concentrated on the outlet side portion 154 so that the concentrated pressure is applied to the outlet side portion 154 of the membrane member 15 and the resilient plate 16 located below the outlet side portion 154 (See the state "b" in FIG. 4). In this instance, if the liquid medicine does not overcome the resilience adjusted by the material and thickness of the resilient plate 16 and/or the thickness of the rib, the outlet side extension portion 176 of the lever 17 located below the resilient plate 16 is not moved. However, when the excess liquid medicine exceeding the flow rate needed for a patient flows into the medicine flow passage 186, it overcomes the resilience of the resilient plate 16 and the outflow pressure of the liquid medicine influences on the outlet side extension portion 176 of the lever 17. In an actual operation, the resilient plate 16 is slightly pressed downward by the outflow pressure of the liquid medicine, and then, presses the outlet side extension portion 176 of the lever 17 (FIG. 4 illustrates a rotated state of the lever 17 but the operational processes are not shown for the sake of convenient illustration and easy understanding). Therefore, the lever 17 rotates in a clockwise direction about the rotary shaft 172 so that the outlet side extension portion 176 of the lever 17 moves downward and the inlet side extension portion 174 of the lever 17 moves upward (See the state "c" in FIG. 4).

After that, the inlet side extension portion 174 of the lever 17 which moves upward presses the inlet side portion 153 of the membrane member 15. As a result, the inlet side portion 153 of the membrane member 15 is pressed and lifted by the inlet side extension portion 174 of the lever 17, and comes into close contact with the lower surface of the upper housing 12 corresponding to the inlet side portion 153 by being expanded and transformed so as to block the medicine inflow hole 184 and shut down the inflow of the liquid medicine (See the state "d" in FIG. 4).

When the inflow of the liquid medicine is blocked as described above, the liquid medicine is not further discharged through the medicine flow passage 186 and the medicine outflow hole 194 as shown in FIG. 5. In this state, the pressure of the liquid medicine applied to the membrane member 15, by the outflow of the liquid medicine, between the lower surface of the upper housing 12 and the upper surface of the outlet side portion 154 disappears so that the pressure of the liquid medicine applied to the resilient plate 16 is also released. Therefore, the resilient plate 16 applies an upward force, i.e. a resiliently restoring force to the membrane member 15 so that the downward force applied to the outlet side extension portion 176 located below the resilient plate 16 is also released (See the state "a" in FIG. 5). In this instance, since the outlet side extension portion 176 is shorter than the inlet side extension portion 174, the lever 17 rotates in a counter-clockwise direction about the rotary shaft 172 by the principle of the seesaw. Accordingly, the inlet side extension portion 174 moves downward and the outlet side extension portion 176 moves upward to release the upward force of the inlet side extension portion 174 pressing the inlet side portion 153 of the membrane member 15 (See the state "b" in FIG. 5).

After that, when the liquid medicine is introduced from the inlet 18 into the medicine flow passage 186 as shown in FIG. 6, the inlet side portion 153 of the membrane member 15 is restored to its original position and shape by the inflow force of the liquid medicine, and then, the liquid medicine is normally injected as shown in FIG. 3. If the liquid medicine is injected excessively again, the steps illustrated in FIGS. 4 to 6 are repeated to repeat blocking of the inflow of the liquid medicine and release of the blocking, and thus to allow the liquid medicine to flow at a constant flow rate.

Figure 7:
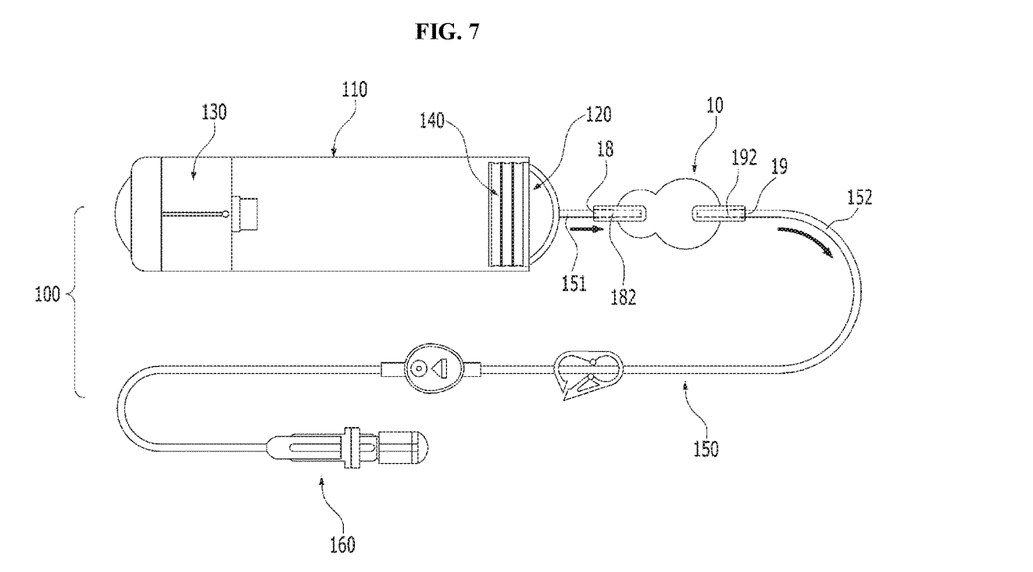
FIG. 7 is a schematic view showing one embodiment of a medicine infusion device to which the regulator for medicine infusion 10 according to an embodiment of the present invention is applied.
Figure 8:
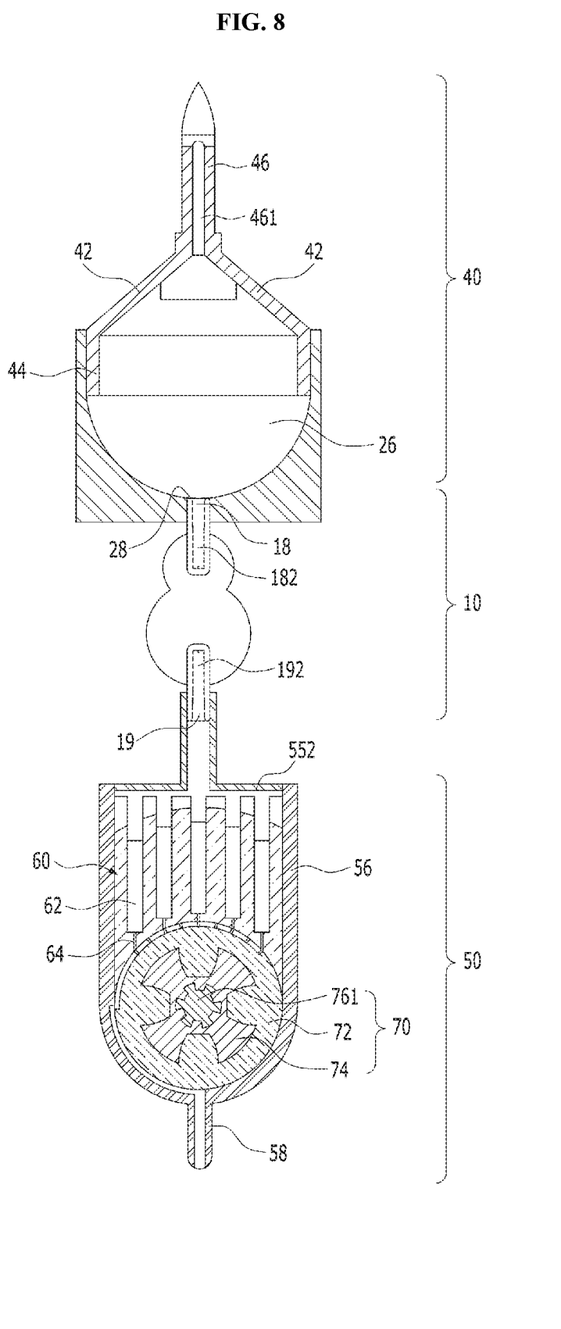
FIG. 8 is a schematic view showing another embodiment of a medicine infusion device to which the regulator for medicine infusion 10 according to an embodiment of the present invention is applied.

Meanwhile, FIGS. 7 and 8 illustrate an example where the regulator 10 for medicine infusion is applied according to an embodiment of the present invention.

For instance, if the regulator 10 for medicine infusion according to the present invention is provided between a medicine storage space 120 inside a cylinder 110 and a tube 150 for connecting an end cap 160, in a medicine injection apparatus 100 as illustrated in PCT Patent Publication No. WO 2010/120051 A2, the regulator 10 can maintain a constant flow rate of the liquid medicine pushed out from the medicine storage space 120 inside the cylinder 110 by a piston 140, without a pressure control valve which controls a gas pressure in a gas supply unit 130 which is disposed at the rear of the piston 140 to supply a gas and to push the piston 140 forward (See FIG. 7). In FIG. 7, the inlet 18 of the regulator 10 according to the present invention is connected with an upstream side tube 151 and the outlet 19 is connected with a downstream side tube 152.

Moreover, if the regulator 10 for medicine infusion according to the present invention is suitably applied to a multi-flow method between an intravenous coupling unit 40 and a multi-flow unit 50 as illustrated in PCT Patent Publication No. WO 2005/105183 A1, it can minimize a change in the flow rate of the liquid medicine discharged at a flow rate selected by rotation of a flow rate control unit 70 in the multi-flow unit 50 (See FIG. 8). That is, if the inlet 18 of the regulator 10 according to the present invention is connected with a medicine inlet 28 of the intravenous coupling unit 40 and branched tubes 552 connected with the outlet 19 are additionally connected with capillary tubes 62 of a capillary member 60, it can select a flow rate by rotation of the flow rate control unit 70 and minimize a change in the selected flow rate. In the meantime, since the components provided in the intravenous coupling unit 40 and the multi-flow unit 50 as illustrated in FIG. 8 are described in PCT Patent Publication No. WO 2005/105183 A1 and an ordinarily skilled person in the art can easily apply them to the present invention, the descriptions of the components and the explanations of the relevant reference numerals will be omitted.

Although the present invention has been described according to the embodiments above, the present invention is not limited to these embodiments. Those skilled in the art will appreciate that various modifications, additions and substitutions are possible, without departing from the scope and spirit of the invention as disclosed in the accompanying claims.

I claim:

1. A regulator for medicine infusion comprising:
a housing having an inlet communicating with an inflow conduit which extends to communicate with a liquid medicine storage space, an outlet communicating with an outflow conduit, and an internal space communicating with the inlet and the outlet;
a membrane member being located in the internal space of the housing and forming a medicine flow passage between the inlet and the outlet, the membrane member receiving a pressure of a liquid medicine discharged via the medicine flow passage from the inlet to the outlet, and the shape of the membrane member being changed by an inflowing force of the liquid medicine itself, which varies depending on a flow rate of the liquid medicine discharged via the medicine flow passage from the inlet to the outlet;
a lever being located below the membrane member and having an inlet side extension portion and an outlet side extension portion opposed to each other with respect to a rotary axis, the inlet side extension portion in contact with a lower surface of the membrane member and rotating on the rotary axis by an inflowing force of the liquid medicine itself, which varies according to the flow rate of the liquid medicine discharged via the medicine flow passage from the inlet to the outlet, to change the shape of the membrane member so that the shape changed membrane member blocks or opens the inlet; and
a resilient plate being located between the membrane member and the lever and being in close contact with both the membrane member and the lever, the resilience of the resilient plate being adjusted so as to allow the pressure of the liquid medicine received through the membrane member to be delivered to the outlet side extension portion of the lever only when the flow rate of the liquid medicine exceeds a predetermined flow rate needed for a patient.

2. The regulator according to claim 1, wherein the membrane member is divided into an inlet side portion and an outlet side portion, and wherein a boundary protrusion portion is formed between the inlet side portion and the outlet side portion of the membrane member.

3. The regulator according to claim 2, wherein an area of the outlet side portion of the membrane member is formed to be larger than that of the inlet side portion of the membrane member in order to make the pressure of the liquid medicine be biasedly applied to the outlet side extension portion of the lever.

4. The regulator according to claim 2, wherein the outlet side portion of the membrane member is formed to be thicker than the inlet side portion of the membrane member in order to make the pressure of the liquid medicine be biasedly applied to the outlet side extension portion of the lever.

5. The regulator according to claim 1, wherein the housing includes an upper housing and a lower housing which are detachably coupled, and the upper housing is configured to form an inflow passage between the inlet and the medicine flow passage and to form an outflow passage between the outlet and the medicine flow passage.

6. The regulator according to claim 5, wherein the inflow passage and the outflow passage are vertically spaced apart from the medicine flow passage, and wherein the inflow passage and the outflow passage are vertically connected to the medicine flow passage through a medicine inflow hole and a medicine outflow hole respectively which are formed opposite to each other in the upper housing.

7. The regulator according to claim 1, wherein the resilient plate includes a peripheral portion, a central portion and a rib for connecting the peripheral portion and the central portion with each other.

8. The regulator according to claim 7, wherein the resilience of the resilient plate is adjusted by at least one selected from the group consisting of a material of the resilient plate, thickness of the resilient plate and thickness of the rib, or the resilience of the membrane member is adjusted by thickness of the outlet side portion of the membrane member, in order to regulate the flow rate and pressure of the liquid medicine discharged via the medicine flow passage from the inlet to the outlet.

9. The regulator according to claim 1, wherein the membrane member is made of silicone, and wherein the resilient plate is made of a plastic material or spring steel.

10. A medicine infusion device comprising a regulator for medicine infusion, the regulator comprising:
a housing having an inlet communicating with an inflow conduit which extends to communicate with a liquid medicine storage space, an outlet communicating with an outflow conduit, and an internal space communicating with the inlet and the outlet;
a membrane member being located in the internal space of the housing and forming a medicine flow passage between the inlet and the outlet, the membrane member receiving a pressure of a liquid medicine discharged via the medicine flow passage from the inlet to the outlet, and the shape of the membrane member being changed by an inflowing force of the liquid medicine itself, which varies depending on a flow rate of the liquid medicine discharged via the medicine flow passage from the inlet to the outlet;
a lever being located below the membrane member and having an inlet side extension portion and an outlet side extension portion opposed to each other with respect to a rotary axis, the inlet side extension portion in contact with a lower surface of the membrane member and rotating on the rotary axis by an inflowing force of the liquid medicine itself, which varies according to the flow rate of the liquid medicine discharged via the medicine flow passage from the inlet to the outlet, to change the shape of the membrane member so that the shape changed membrane member blocks or opens the inlet; and
a resilient plate being located between the membrane member and the lever and being in close contact with both the membrane member and the lever, the resilience of the resilient plate being adjusted so as to allow the pressure of the liquid medicine received through the membrane member to be delivered to the outlet side extension portion of the lever only when the flow rate of the liquid medicine exceeds a predetermined flow rate needed for a patient.

11. The medicine infusion device according to claim 10, wherein the membrane member is divided into an inlet side portion and an outlet side portion, and wherein a boundary protrusion portion is formed between the inlet side portion and the outlet side portion of the membrane member.

12. The medicine infusion device according to claim 11, wherein an area of the outlet side portion of the membrane member is formed to be larger than that of the inlet side portion of the membrane member in order to make the pressure of the liquid medicine be biasedly applied to the outlet side extension portion of the lever.

13. The medicine infusion device according to claim 11, wherein the outlet side portion of the membrane member is formed to be thicker than the inlet side portion of the membrane member in order to make the pressure of the liquid medicine be biasedly applied to the outlet side extension portion of the lever.

14. The medicine infusion device according to claim 10, wherein the housing includes an upper housing and a lower housing which are detachably coupled, and the upper housing is configured to form an inflow passage between the inlet and the medicine flow passage and to form an outflow passage between the outlet and the medicine flow passage.

15. The medicine infusion device according to claim 14, wherein the inflow passage and the outflow passage are vertically spaced apart from the medicine flow passage, and wherein the inflow passage and the outflow passage are vertically connected to the medicine flow passage through a medicine inflow hole and a medicine outflow hole respectively which are formed opposite to each other in the upper housing.

16. The medicine infusion device according to claim 10, wherein the resilient plate includes a peripheral portion, a central portion and a rib for connecting the peripheral portion and the central portion with each other.

17. The medicine infusion device according to claim 16, wherein the resilience of the resilient plate is adjusted by at least one selected from the group consisting of a material of the resilient plate, thickness of the resilient plate and thickness of the rib, or the resilience of the membrane member is adjusted by thickness of the outlet side portion of the membrane member, in order to regulate the flow rate and pressure of the liquid medicine discharged via the medicine flow passage from the inlet to the outlet.

18. The medicine infusion device according to claim 10, wherein the membrane member is made of silicone, and wherein the resilient plate is made of a plastic material or spring steel.

* * * * *